United States Defensive Publication [19] (H) [11] T104,903

Lok et al. [43] Dec. 4, 1984

[54] PHOTOGRAPHIC SPEED INCREASING AND LATENT IMAGE STABILIZING COMPOUNDS

[76] Inventors: Roger Lok; John P. Freeman; William H. Baum, all of Kodak Park, Rochester, N.Y. 14650

[21] Appl. No.: 577,934

[22] Filed: Feb. 7, 1984

Related U.S. Application Data

[60] Division of Ser. No. 466,244, Feb. 14, 1983, Pat. No. 4,451,557, which is a continuation-in-part of Ser. No. 320,794, Nov. 12, 1981, Pat. No. 4,378,426.

[51] Int. Cl.[3] ..... C07D 515/00; C07D 233/30

[52] U.S. Cl. ..... 260/239 R; 548/120; 548/190; 548/202; 548/217; 548/222; 548/233; 548/323; 548/337; 548/342

[57] ABSTRACT

Photographic silver halide emulsions show increased speed and reduced latent image fading when a compound of the following structure is incorporated:

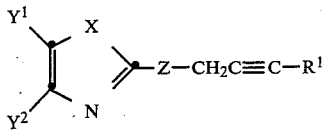

wherein:

X is $$-O-,\ -S-,\ -Se-,\ \text{or}\ -\overset{R}{N}-;$$

$Y^1$ and $Y^2$ individually represent hydrogen or an aromatic nucleus or together represent the atoms completing a fused aromatic nucleus;

Z is $$-CH_2\overset{R}{N}-\ \text{or}\ -\overset{R}{N}-;$$

R is hydrogen or lower alkyl of from 1 to 5 carbon atoms; and $R^1$ is hydrogen or methyl.

2 Claims, No Sheets Drawing,

24 Pages Specification

The file of this unexamined application may be inspected and copies thereof may be purchased (849 O.G. 1221, Apr. 9, 1968).